US012642709B2

(12) United States Patent (10) Patent No.: US 12,642,709 B2
Iwamura (45) Date of Patent: Jun. 2, 2026

(54) APPARATUS AND METHOD FOR MANUFACTURING ABSORBENT CORE FOR DISPOSABLE WEARABLE ARTICLES

(71) Applicant: ZUIKO CORPORATION, Ibaraki (JP)

(72) Inventor: Yosuke Iwamura, Ibaraki (JP)

(73) Assignee: ZUIKO CORPORATION, Ibaraki (JP)

( * ) Notice: Subject to any disclaimer, the term of this patent is extended or adjusted under 35 U.S.C. 154(b) by 291 days.

(21) Appl. No.: 18/700,077

(22) PCT Filed: Oct. 3, 2022

(86) PCT No.: PCT/JP2022/036954
§ 371 (c)(1),
(2) Date: Dec. 19, 2024

(87) PCT Pub. No.: WO2023/063143
PCT Pub. Date: Apr. 20, 2023

(65) Prior Publication Data
US 2025/0114251 A1 Apr. 10, 2025

(30) Foreign Application Priority Data

Oct. 15, 2021 (JP) ................................. 2021-169291

(51) Int. Cl.
*A61F 13/15* (2006.01)
(52) U.S. Cl.
CPC .. *A61F 13/15772* (2013.01); *A61F 13/15626* (2013.01); *A61F 13/15642* (2013.01);
(Continued)
(58) Field of Classification Search
None
See application file for complete search history.

(56) References Cited

U.S. PATENT DOCUMENTS

| | | | |
|---|---|---|---|
| 4,764,325 A | 8/1988 | Angstadt | |
| 2013/0305511 A1* | 11/2013 | Schoultz | ........... A61F 13/15756 |
| | | | 29/700 |

(Continued)

FOREIGN PATENT DOCUMENTS

| | | | |
|---|---|---|---|
| JP | 2541558 B2 | 10/1996 | |
| JP | 3153060 B2 | 4/2001 | |

(Continued)

OTHER PUBLICATIONS

English-language translation of International Preliminary Report on Patentability/Written Opinion issued in connection with underlying International Application PCT/JP2022/036954.
(Continued)

*Primary Examiner* — Barbara J Musser
(74) *Attorney, Agent, or Firm* — United IP Counselors, LLC

(57) ABSTRACT

An apparatus for manufacturing an absorbent core includes: a first drum that has a first area for sucking and stacking fibers on an outer peripheral portion of the first drum and stack a first core portion in the first area; and a second drum that has a plurality of second areas, smaller than the first area, for sucking and stacking the fibers on an outer peripheral portion of the second drum and that successively transfers second core portions stacked in each of the second areas to the first drum, wherein the second drum is rotated at a high first circumferential velocity when the second drum transfers each of the second core portions and, the second drum is rotated at a second circumferential velocity, lower than the first circumferential velocity, in non-transfer time, which is after the transfer and until subsequent transfer.

14 Claims, 5 Drawing Sheets

(52) U.S. Cl.
　　CPC .................. *A61F 13/15764* (2013.01); *A61F*
　　　　　　　　　　　　　　　*2013/15943* (2013.01)

(56) References Cited

U.S. PATENT DOCUMENTS

| | | | |
|---|---|---|---|
| 2019/0175423 A1 * | 6/2019 | Inoue ...................... | A61F 13/15 |
| 2022/0211549 A1 | 7/2022 | Umebayashi et al. | |

FOREIGN PATENT DOCUMENTS

| | | | |
|---|---|---|---|
| JP | 2009112438 | A | 5/2009 |
| JP | 4312112 | B2 | 8/2009 |
| WO | 2020209006 | A1 | 10/2020 |

OTHER PUBLICATIONS

English-language translation of International Search Report issued in connection with underlying International Application PCT/JP2022/036954.

* cited by examiner

FIG. 1A                                            FIG. 1B

APPARATUS AND METHOD FOR MANUFACTURING ABSORBENT CORE FOR DISPOSABLE WEARABLE ARTICLES

TECHNICAL FIELD

The present invention relates to an apparatus and method for manufacturing an absorbent core for disposable wearable articles.

BACKGROUND ART

Conventionally, in absorbent articles such as diapers, a region with different thicknesses is formed in a portion of an absorbent core. In one method for producing such an absorbent core, an absorbent core having a thick portion is produced by using two fiber stacking drums as follows. In this method, a first absorption layer is formed by one fiber stacking drum, a second absorption layer having a smaller area than the first absorption layer is formed by the other fiber stacking drum, and the two absorption layers are superposed (Patent Document 1).

In another method, an absorbent core having a thick portion is formed by fitting a thick core into a hole formed in thin cores (Patent Document 2).

CITATION LIST

Patent Literature

Patent Document 1: Japanese Patent No. 2,541,558 (FIG. 1)
Patent Document 2: WP 2020/209006 A1 (front page)

SUMMARY OF THE INVENTION

In the prior art, the thick portion has a small area compared with the thin portion. For that reason, the fiber stacking areas on the drum corresponding to the thick portions are small and the flow rate of the air flowing toward the drum is also small. In that case, there is a problem that, in a defibrator that grinds pulp to generate fibers, an unnecessary rise in temperature occurs due to the small flow rate and the fibers are likely to be burned (scorched).

Furthermore, the thick portion is partially provided relative to the entire absorbent core. For that reason, the fiber stacking areas corresponding to those portions are provided intermittently and in a small size on the outer peripheral surface of the entire drum, the ratio of the areas to the entire drum is small, and fiber stacking unevenness is likely to occur. As a result, unevenness is likely to occur in the absorbent core.

Consequently, an object of the present invention is to provide an apparatus and method for manufacturing an absorbent core that reduces a rise in temperature in a crusher to prevent scorching of fibers and with which unevenness in the absorbent core is less likely to occur.

The apparatus of the present invention is an apparatus for manufacturing an absorbent core C for disposable wearable articles by combining a first core portion C1 and second core portions C2, the apparatus comprising:
  a feeder 3 having a defibrator 33 configured to generate fibers F crushed into a fibrous form and feed the fibers F;
  a first drum 1 having a first area α1 for sucking and stacking the fibers F on an outer peripheral portion 10 of the first drum 1, the first drum 1 being configured to stack a first core portion C1 in the first area α1;
  a second drum 2 having a plurality of second areas α2, smaller than the first area α1, for sucking and stacking the fibers F on an outer peripheral portion 20 of the second drum 2, the second drum 2 being configured to successively transfer second core portions C2 stacked in each of the second areas α2 to the first drum 1; and
  a variable speed drive 5 configured to rotate the second drum 2 at a high first circumferential velocity V1 when the second drum 2 transfers each of the second core portions C2 and, rotate the second drum 2 at a second circumferential velocity V2, lower than the first circumferential velocity V1, in non-transfer time, which is after the transfers and until subsequent transfers.

The method of the present invention is a method of manufacturing an absorbent core C for a disposable wearable article by combining a first core portion C1 and a second core portion C2, the method using
  a feeder 3 having a defibrator 33 configured to generate fibers F crushed into a fibrous form and feed the fibers F,
  a first drum 1 having a first area α1 for sucking and stacking the fibers F on an outer peripheral portion 10 of the first drum 1, the first drum 1 being configured to stack a first core portion C1 in the first area α1, and
  a second drum 2 having a plurality of second areas α2, smaller than the first area α1, for sucking and stacking the fibers F on an outer peripheral portion 20 of the second drum 2, the second drum 2 being configured to successively transfer second core portions C2 stacked in each of the second areas α2 to the first drum 1,
  the method comprising:
  a step of stacking the first core portion C1 in the first area α1;
  a step of stacking the second core portions C2 in the second areas α2;
  a step of transferring the second core portions C2 from the second drum 2 onto the first drum 1;
  a step of rotating the second drum 2 at a high first circumferential velocity V1 during the transferring; and
  a step of rotating the second drum 2 at a second circumferential velocity V2 lower than the first circumferential velocity V1 in non-transfer time.

According to these inventions, the second drum 2 that generates the second core portions rotates at the low second circumferential velocity V2 at the non-transfer time. For that reason, the pitch between the second core portions that are transferred becomes larger on the first drum, so that the second core portions become repitched. For that reason, the second areas can be densely formed on the second drum.

In this way, as the second areas for the second core portions can be densely provided on the second drum, the flow rate of the air thus also increases, whereby a rise in temperature in the defibrator 33 can be inhibited. As a result, the fibers are less likely to be scorched.

Furthermore, because the second areas are densely provided on the second drum, fiber stacking unevenness is less likely to occur.

BRIEF DESCRIPTION OF THE DRAWINGS

FIG. 1A is a conceptual side view showing Embodiment 1 of the manufacturing apparatus and method, FIG. 1B is a flattened view showing areas of a second drum.

DESCRIPTION OF EMBODIMENTS

Figure 1C:
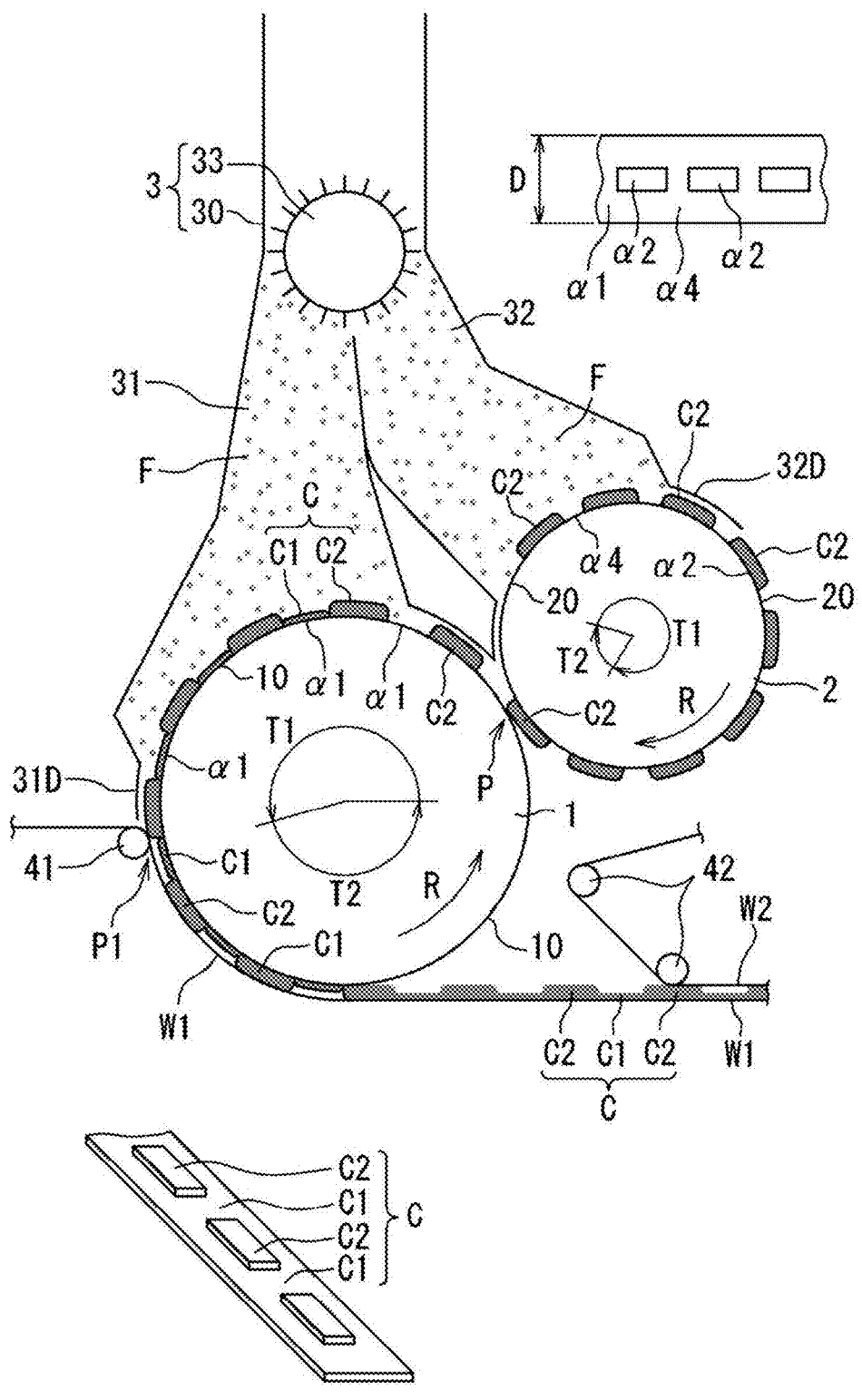
FIG. 1C is a perspective view of an absorbent core.

In the apparatus of the present invention, the variable speed drive 5 preferably includes a servomotor 50 that rotates the second drum 2 and a controller 51 that controls the rotation of the servomotor 50. In this case, control of the periodic changes in velocity becomes easy.

In the apparatus of the present invention, the controller 51 preferably controls the rotation of the servomotor 50 so that the high first circumferential velocity V1 of the second drum 2 during the transfer is same with the circumferential velocity of the first drum 1.

Meanwhile, in the method of the present invention, the second drum 2 is preferably rotated so that the high first circumferential velocity V1 of the second drum 2 during the transfer is same with the circumferential velocity of the first drum 1.

In these cases, as the circumferential velocities of the two drums at the transfer time (during the transfer) are mutually equal, problems such as the second core portions losing their shape at the transfer time are less likely to occur.

In the apparatus of the present invention, more preferably, the controller 51 controls the rotation of the servomotor 50 so that the high first circumferential velocity V1 during the transfer is a constant circumferential velocity, and in the non-transfer time, the rotation of the second drum 2 is decelerated from the first circumferential velocity V1 to the low second circumferential velocity V2 after the transfer and the rotation of the second drum 2 is accelerated from the low second circumferential velocity V2 to the high first circumferential velocity V1 before subsequent transfer.

Meanwhile, in the method of the present invention, more preferably, the rotation of the servomotor 50 is controlled so that the high first circumferential velocity V1 during the transfer is a constant circumferential velocity, and in the non-transfer time, the rotation of the second drum 2 is decelerated from the first circumferential velocity V1 to the low second circumferential velocity V2 after the transfer and the rotation of the second drum 2 is accelerated from the low second circumferential velocity V2 to the high first circumferential velocity V1 before subsequent transfer.

In these cases, the second drum is decelerated and accelerated at the non-transfer time and the second drum rotates at a constant velocity during the transfer, so the velocity of the second drum can be periodically changed without problems such as the second core portions losing their shape during the transfers occurring.

In the apparatus of the present invention, the feeder 3 may have a single defibrator as the defibrator 33 and include a first duct portion 31 configured to gas-transporting the fibers F generated by the single defibrator 33 to the first drum 1 and a second duct portion 32 configured to gas-transporting the fibers F generated by the single defibrator 33 to the second drum 2.

Meanwhile, the method of the present invention may further comprise a step of gas-transporting the fibers F generated by a single defibrator 33 through a first duct portion 31 to the first drum 1 and a step of gas-transporting the fibers F generated by the single defibrator 33 through a second duct portion 32 to the second drum 2.

Any feature described and/or illustrated in conjunction with one of the above aspects or the following embodiments may be used in the same or similar form in one or more of other aspects or other embodiments, and/or may be used in combination with, or in place of, any feature of the other aspects or embodiments.

The present invention will become more clearly understood from the following description of preferred embodiments taken in conjunction with the accompanying figures. However, the embodiments and the figures are merely for the purposes of illustration and explanation and should not be utilized to define the scope of the present invention. The scope of the present invention shall be defined only by the claims. In the accompanying figures, like parts numbers in multiple figures refer to the same or corresponding parts.

It will be noted that some katakana notations in the present specification are accompanied by English words in parentheses to make their meanings clearer.

EMBODIMENTS

Embodiments of the present invention will be described below in accordance with the drawings.

The absorbent core manufactured by the manufacturing apparatus may, for example, be used as a core for disposable underwear and diapers as well as incontinence pads and have, for example, an hourglass shape in plan view.

Figure 2A:
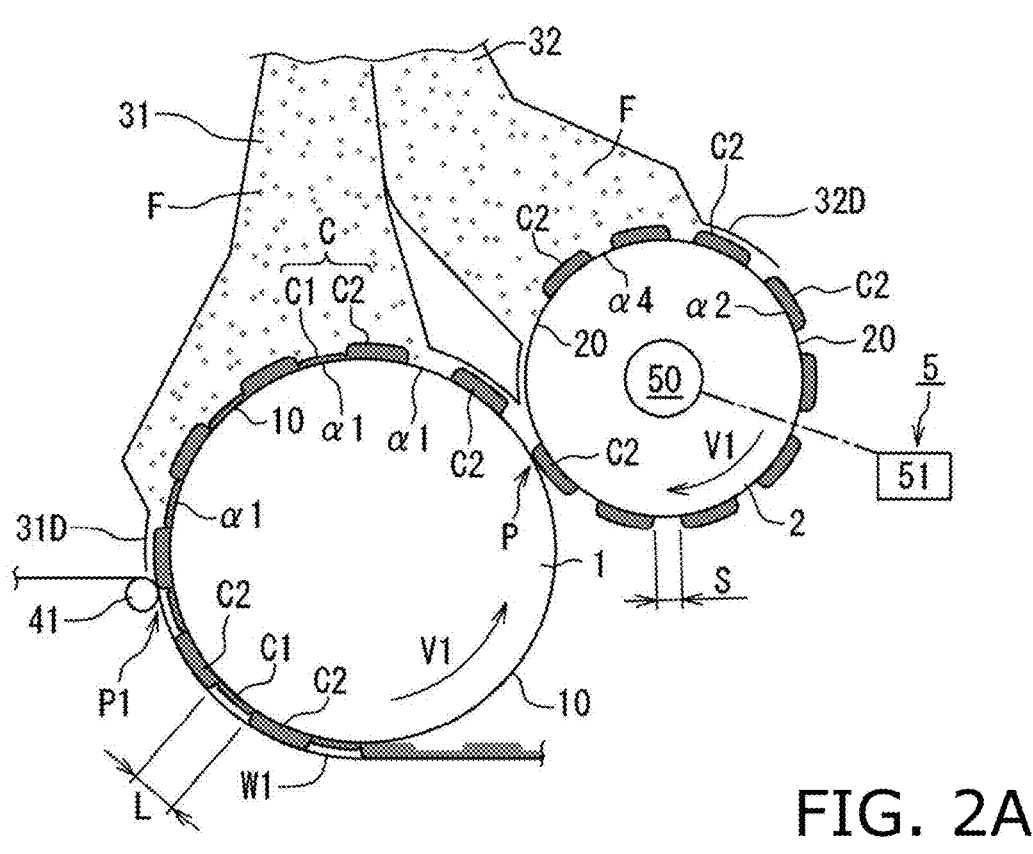
FIG. 2A and FIG. 2B are conceptual side views showing two drums in states at a transfer time and a non-transfer time, respectively.
Figure 2B:
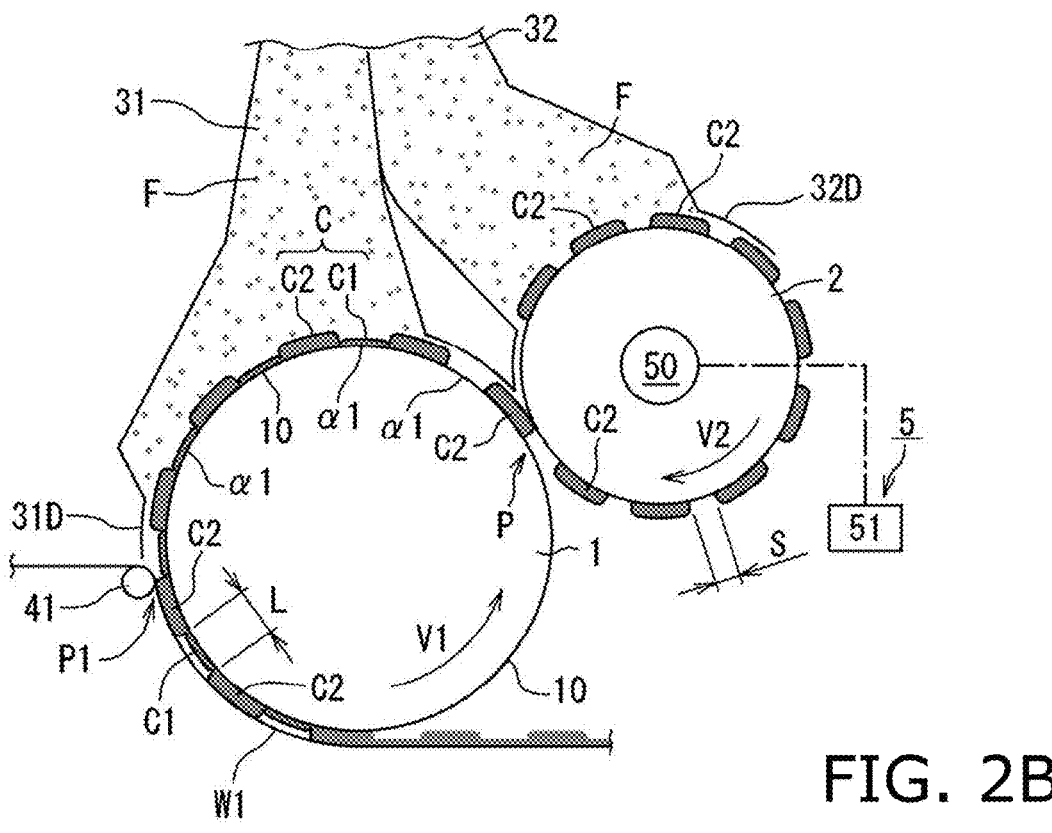

FIG. 1A, FIG. 2A, and FIG. 2B show Embodiment 1.

As shown in FIG. 1A, the manufacturing apparatus includes a feeder 3 and first and second drums 1, 2.

The feeder 3 includes a cylindrical case 30 and a defibrator 33. The defibrator 33 defibrates (crushes) pulp, fed from upstream, into a fibrous form to generate fluff pulp (fibers). The fluff pulp fills the case 30, travels through first and second duct portions 31, 32, and is stacked on outer peripheral portions 10, 20 of the first and second drums 1, 2 because of suction chambers (not shown in the drawings) in the first and second drums 1, 2 being set to a negative pressure. This kind of defibration and fiber stacking is a well-known art and disclosed in JP2009-112438A for example.

It will be noted that as a material configuring the absorbent core, a particulate material of a polymer compound having a high absorption capacity called SAP (superabsorbent polymer particles) may be added.

The first and second drums 1, 2 are substantially cylindrical and, as is well known, are formed of a plurality of segments (not shown in the drawings). The first and second drums 1, 2 are provided in correspondence to the first and second duct portions 31, 32. The drums 1, 2 continuously rotate in circumferential directions R and simultaneously suck, from the outer peripheral portions 10, 20 of the drums 1, 2 toward the inside suction chambers (not shown in the drawings), fibers F fed from the feeder 3, whereby the fibers F are continuously stacked on the outer peripheral portions 10, 20 in predetermined first or second areas α1, α2.

The suction chambers are disposed in predetermined suction zones T1 in the circumferential directions R of the drums 1, 2 and are connected to negative pressure sources (not shown in the drawings) so that the insides of the suction chambers have a negative pressure. Each of the suction chambers is disposed in proximity to the inner peripheral sides of the outer peripheral portions 10, 20 of the drums 1, 2. Consequently, in the suction zones T1, the fibers are stacked and are sucked and held on the drums 1, 2.

At the same time, each of the drums 1, 2 is provided with a non-suction zone T2 where the outer peripheral portion 10, 20 of the drum does not face the suction chamber.

In the case of the present embodiment, a first area α1 of the first drum 1 is continuous in the circumferential direction R of the first drum 1. By contrast, second areas α2 of the second drum 2 are intermittently provided at regular intervals in the circumferential direction R of the second drum 2. Portions of each of the areas α1, α2 are ordinarily fiber stacking recesses. The basic or specific structures of these recesses and drums are well known and disclosed, for example, in Japanese Patent No. 2,541,558, Japanese Patent No. 4,312,112, and Japanese Patent No. 3,153,060.

As shown in FIG. 1B, the second areas α2 are provided in such a way as to be contained in the first area α1. For example, in the case of the present embodiment, the intermittently provided second areas α2 are small in both the circumferential direction R and a width direction D relative to the continuously provided first area α1 and are provided in such a way as to be contained in the continuously provided first area α1. In the second drum 2 shown in FIG. 1A, the region of the outer peripheral portion 20 outside the second areas 2 is a blocking area α4 where stacking of the fibers F is blocked.

It will be noted that the first area α1 may, for example, have an hourglass shape when flattened in a plane and be discontinuous.

In the first area α1 shown in FIG. 1B, a thin portion (an example of a first core portion) C1, shown in FIG. 1C, is formed. In the second areas α2 shown in FIG. 1B, thick portions (an example of second core portions) C2, shown in FIG. 1C, are formed.

The first and second duct portions 31, 32 shown in FIG. 1A are connected to the case 30 of the feeder 3 and guide the fibers F from the feeder 3 to the outer peripheral portion 10 of the first drum 1 and the outer peripheral portion 20 of the second drum 2, respectively. Portions of the outer peripheral portions 10, 20 of the first and second drums 1, 2 face the ends of the first and second duct portions 31, 32, respectively.

At least a portion of the suction zone T1 of each of the drums 10, 20 faces an opening in the end of each of the duct portions 31, 32. It will be noted that domes 31D, 32D extending along the drums may be formed in the ends of the duct portions.

The thick portions C2 are bulkier and thicker than the thin portion C1. This kind of difference in thickness between the thin portion C1 and the thick portions C2 is obtained by, for example, differentiating the magnitudes of the negative pressure in the suction chambers and/or their suction periods.

The first drum 1 and the second drum 2 are in contact with each other via the thick portions C2 at a transfer point P. At the transfer point P, the first drum 1 is set to the suction zone T1 while the second drum 2 is set to the non-suction zone T2.

It will be noted that the first drum 1 and the second drum 2 may be in close enough proximity so that the thick portions C2 can be transferred from the second drum 2 to the first drum 1 even if the first drum 1 and the second drum 2 are not in contact via the thick portions C2.

Downstream of the first drum 1 is provided a first transport unit 41 that transports a first web W1 (a carrier web) for transporting an absorbent core C formed by the thin portion C1 and the thick portions C2. Further downstream of the first transport unit 41 is provided a second transport unit 42 that transports a second web W2 that sandwiches the absorbent core C between itself and the first web W1. It will be noted that the first transport unit 41 transports the first web W1 along the first drum 1 so as to sandwich the absorbent core C between the first web W1 and the first drum 1.

The transport units 41, 42 may include, in addition to guide rollers, unwind rollers that unwind the webs and an anvil roll that transports and cuts the absorbent core C sandwiched between the pair of webs. It will be noted that the webs may be water-absorbent and water-permeable.

The transfer point P is a point that is provided between the first duct portion 31 and the second duct portion 32 and at which the first drum 1 and the second drum 2 are in contact with each other via the thick portions C2 and at which the thick portions C2 stacked in the second areas α2 are transferred from the second drum 2 to an area on the first drum 1 where the thin portion C1 is not formed.

The feeder 3 includes a single defibrator 33. The first duct portion 31 gas-transports the fibers F generated by the single defibrator 33 to the first drum 1. The second duct portion 32 gas-transports the fibers F generated by the single defibrator 33 to the second drum 2.

Next, a variable speed drive 5 will be described using FIG. 2A, FIG. 2B, and FIG. 5.

In FIG. 2A, the variable speed drive 5 includes a servomotor 50 that rotates the second drum 2 and a controller 51 that controls the rotation of the servomotor 50. The controller 51 controls the rotation of the servomotor 50 so that a high first circumferential velocity V1 of the second drum 2 at the transfer time is same with the circumferential velocity of the first drum 1.

Figure 5:
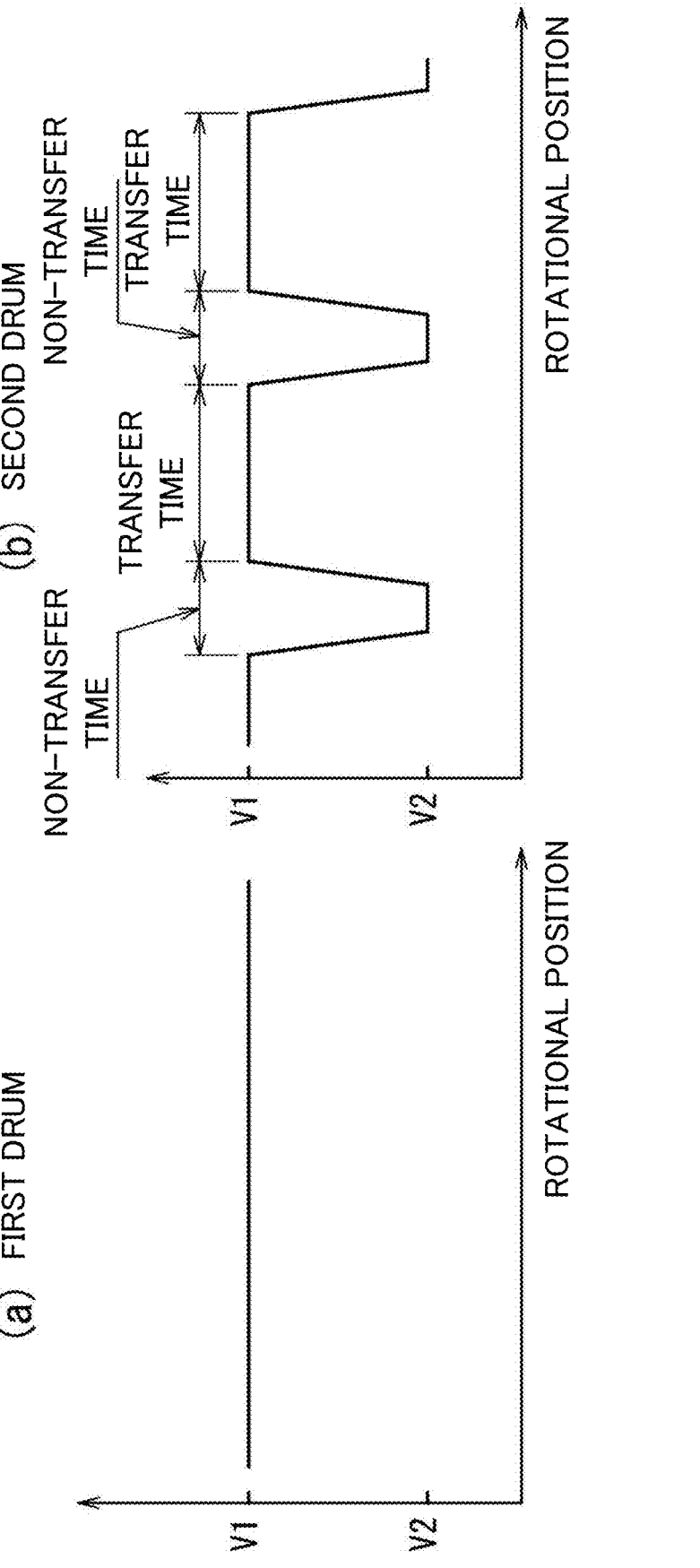
FIG. 5(a) and FIG. 5(b) are velocity diagrams of a first drum and a second drum, respectively.

The variable speed drive 5 controls the rotation of the servomotor 50 so that the high first circumferential velocity V1 at the transfer time (during the transfer) in FIG. 5 (b) is a constant circumferential velocity. Meanwhile, the controller 51 shown in FIG. 2B controls the rotation of the servomotor 50 so that, in the non-transfer time shown in FIG. 5 (b), the second drum 2 decelerates from the first circumferential velocity V1 to a low second circumferential velocity V2 after the transfer and the second drum 2 accelerates from the low second circumferential velocity V2 to the high first circumferential velocity V1 before subsequent transfer.

In the case of the present embodiment, the circumferential velocity of the first drum 1 in FIG. 5 (a) may be maintained at a high constant circumferential velocity V1.

Next, the method of manufacturing the absorbent core C will be described.

In FIG. 1, a portion of the fibers F generated by the single defibrator 33 is gas-transported through the first duct portion 31 to the outer peripheral portion 10 of the first drum 1. Furthermore, another portion of the fibers F generated by the single defibrator 33 is gas-transported through the second duct portion 32 to the outer peripheral portion 20 of the second drum 2.

When the second drum 2 faces the second duct portion 32 in the suction zone T1, the fibers F generated by the feeder 3 are stacked in the second areas α2, whereby the thick portions C2 are stacked at regular intervals on the outer peripheral portion 20 of the second drum 2. The thick portions C2 are transported to the transfer point P in a state in which they are sucked in the second areas α2 of the second drum 2.

At the transfer point P, the thick portions C2 are transferred from the second drum 2 onto the first area α1 of the first drum 1. That is, at the transfer point P, the second drum 2 is set to the non-suction zone T2 while the first drum 1 is set to the suction zone T1.

Consequently, the thick portions C2 on the second drum 2 are transferred to and disposed on a portion of the first area α1 of the first drum 1.

It will be noted that, in the case of the present embodiment, the thick portions C2 are sucked and disposed on (transferred to) a portion of the first area α1 in a state in which the fibers F are not being stacked in the first area α1.

As shown in FIG. 5, the second drum 2 rotates at the high first circumferential velocity V1 during the transfer (at the transfer time). That is, the second drum 2 is rotated so that the first circumferential velocity V1 of the second drum 2 is same with the circumferential velocity of the first drum 1.

Meanwhile, in the non-transfer time, the second drum 2 is rotated at the second circumferential velocity V2 that is lower than the first circumferential velocity V1.

That is, the rotation of the servomotor 50 is controlled so that the high first circumferential velocity V1 of the second drum 2 at the transfer time (during the transfer) is a constant circumferential velocity and so that, in the non-transfer time, the second drum 2 is decelerated from the first circumferential velocity V1 to the low second circumferential velocity V2 after the transfer and the second drum 2 is accelerated from the low second circumferential velocity V2 to the high first circumferential velocity V1 before subsequent transfer.

In this way, the velocity of the second drum 2 shown in FIG. 2A and FIG. 2B is periodically changed, so a spacing S between mutually adjacent thick portions C2 on the second drum 2 increases as indicated by a spacing L after the thick portions C2 have been transferred onto the first drum 1. That is, the thick portions C2 on the second drum 2 can be arranged at a small pitch. Thus, the second areas α2 can be densely arranged on the second drum 2.

When the portions of the first drum 1 that have received the thick portions C2 in FIG. 2B rotate in the circumferential direction R and face the first duct portion 31, the fibers F generated by the feeder 3 are stacked in the first area α1, whereby the continuous thin portion C1 is generated in the portions around the thick portions C2. At this time, the fibers F may also be slightly stacked on the portions of the thick portions C2 in the first area α1.

It will be noted that in the case of the present embodiment, the absorbent core C in which the thin portion C1 is continuous along the outer peripheral portion 10 of the first drum 1 is formed in the step of forming the thin portion C1.

In this way, the absorbent core C shown in FIG. 1C is formed on the outer peripheral portion 10 of the first drum 1. After the formed absorbent core C emerges from the dome 31D of the first duct portion 31, the absorbent core C is transferred to and transported on the first web W1 guided by the first transport unit 41 in the non-suction zone T2.

Thereafter, the absorbent core C is sandwiched between the second web W2 transported by the second transport unit 42 and the first web W1, and then the absorbent core C is cut into units of individual wearable articles.

It will be noted that as shown in FIG. 1C the surfaces of the thick portions C2 of the absorbent core C are formed so as to project beyond the surface of the thin portion C1.

FIG. 3A to FIG. 4B show Embodiment 2.

Regarding Embodiment 2, parts differing from those of Embodiment 1 will be mainly described.

In the case of the present embodiment, the first drum 1 is provided with blocking areas α3, where stacking of the fibers F is blocked, in addition to the first area α1. The blocking areas α3 may, for example, be formed by setting the porosity of a mesh on the outer peripheral portion 10 small so that the suction resulting from negative pressure is weakened. The first drum 1 and the second drum 2 are in contact at the transfer point P in the following kind of state.

That is, the two drums are in contact at the transfer point P so that the thin portion C1 is stacked on the first drum 1 in the first area α1 outside the blocking areas α3 where stacking of the fibers F is blocked and, in a state in which the fibers F are not being stacked in the blocking areas α3, the thick portions C2 stacked on the second drum 2 are transferred from the second drum 2 to the blocking areas α3 of the first drum 1.

Next, the method of manufacturing the absorbent core C of Embodiment 2 will be described.

First, the thin portion C1, whose grammage is lower than that of the thick portions C2, is formed on the first drum 1 in the area of the first area α1 outside the blocking areas α3 where stacking of the fibers F is blocked. At this time, the fibers F need not be stacked in the blocking areas α3.

Meanwhile, the thick portions C2 are formed on the second drum 2 because of the fibers F from the feeder 3 being stacked in the second areas α2. At this time, the thick portions C2 are formed on the second drum 2 so as to match the planar shape of the blocking areas α3 of the first drum 1.

Figures 3A, 3B, 3C:
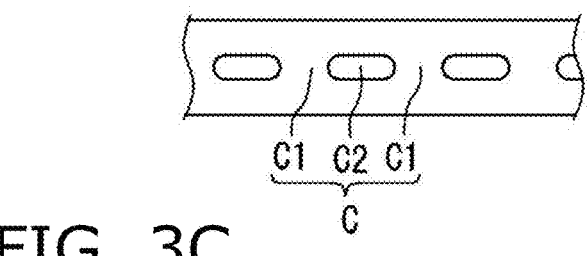
FIG. 3A is a conceptual side view showing Embodiment 2 of the manufacturing apparatus and method.
FIG. 3B is a flattened view showing areas of a first drum.
FIG. 3C is a plan view of an absorbent core.
Figure 4A:
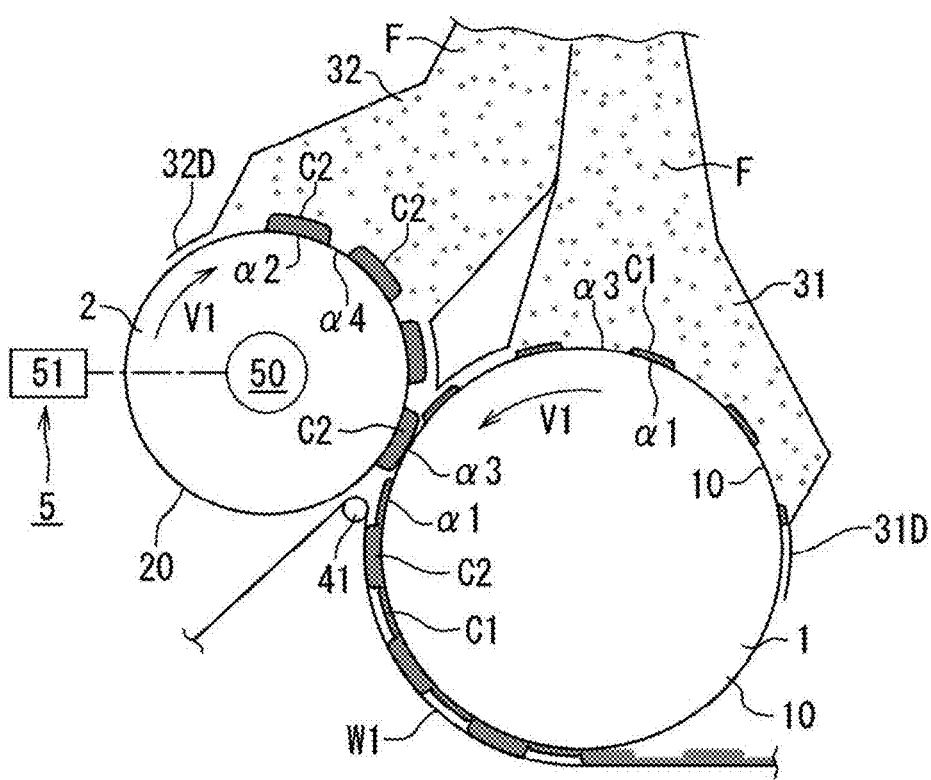
FIG. 4A and FIG. 4B are conceptual side views showing two drums in states at a transfer time and a non-transfer time, respectively.
Figure 4B:
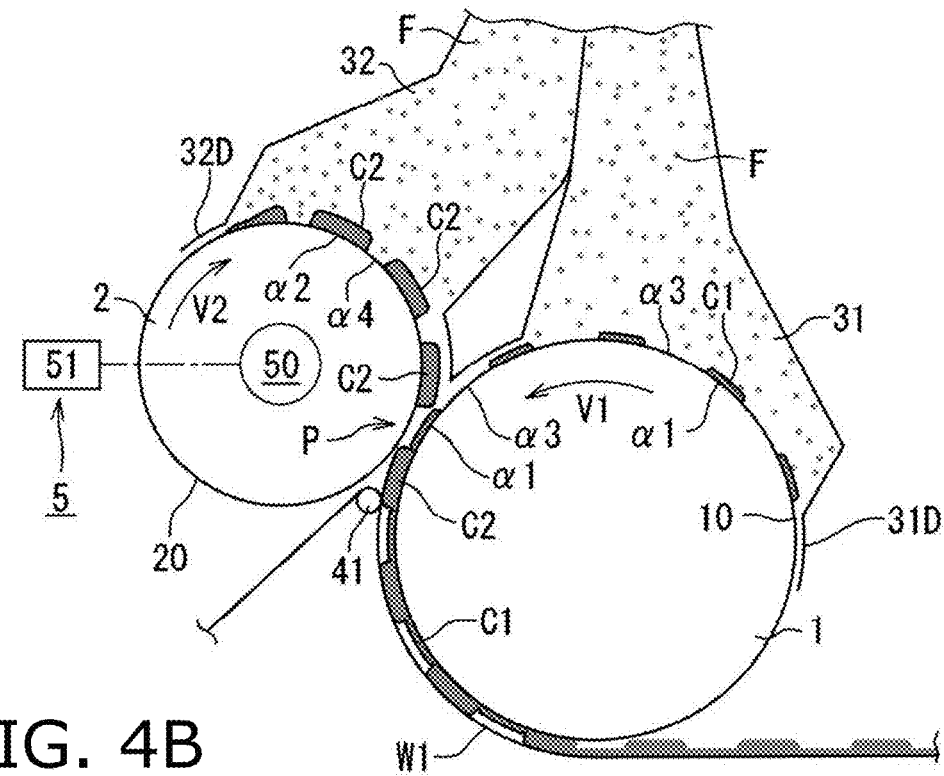

Thereafter, at the transfer point P, the thick portions C2 on the second drum 2 are disposed in the blocking areas α3 of the first drum 1, and the thick portions C2 become mated with the thin portion C1. In this way, the absorbent core C of FIG. 3C is generated, and the continuous absorbent core C sandwiched between the pair of webs W1, W2 is generated in the same way as in Embodiment 1 above.

In this example also, the second drum 2 is rotated at the high first circumferential velocity V1 when the second drum 2 is transferring each of the thick portions C2 (during the transfer). After the transfer, the second drum 2 is rotated at the second circumferential velocity V2 that is lower than the first circumferential velocity V1 at the non-transfer time until subsequent transfer.

Consequently, the pitch between the plural thick portions C2 is small on the second drum 2 and becomes larger on the first drum 1. That is, the second areas α2 of the second drum 2 can be densely arranged at a small pitch.

Incidentally, although in each of the above embodiments the circumferential velocity of the first drum 1 is constant, the circumferential velocity may be decreased or increased after the transfer and until subsequent transfer, i.e., in the non-transfer time.

Incidentally, although in each of the above embodiments the thick portions C2 and the thin portion C1 have shapes that mate, they need not necessarily be configured in this way. For example, the absorbent core may be formed by forming a thin and uniform first core portion with the first drum and layering on the first core portion discontinuous second core portions formed with the second drum.

While preferred embodiments have been described above with reference to the drawings, a variety of obvious changes and modifications will readily occur to those skilled in the art upon reading the present specification.

For example, the absorbent core may include SAP.

Furthermore, the absorbent core C may be formed on the drums in a discontinuous state in the circumferential direction R.

Consequently, such changes and modifications are to be interpreted as being within the scope of the present invention as defined by the claims.

INDUSTRIAL APPLICABILITY

The present invention can be applied to the manufacture of an absorbent core for disposable wearable articles.

REFERENCE SIGNS LIST

1: First Drum
10: Outer Peripheral Portion
2: Second Drum
20: Outer Peripheral Portion
3: Feeder
31: First Duct Portion
32: Second Duct Portion
31D, 32D: Domes
33: Defibrator
41: First Transport Unit
42: Second Transport Unit
5: Variable Speed Drive
50: Servomotor
51: Controller
C: Absorbent Core
C1: Thin Portion (example of First Core Portion)
C2: Thick Portions (example of Second Core Portions)
D: Width Direction
P: Transfer Point
F: Fibers
R: Circumferential Direction
S, L: Spacings
T1: Suction Zones
T2: Non-suction Zones
$\alpha 1$: First Area
$\alpha 2$: Second Areas
$\alpha 3$: Blocking Areas
$\alpha 4$: Blocking Area

The invention claimed is:

1. An apparatus for manufacturing an absorbent core for disposable wearable articles by combining a first core portion and second core portions, the apparatus comprising:
   a feeder having a defibrator configured to generate fibers crushed into a fibrous form and feed the fibers;
   a first drum having a first area for sucking and stacking the fibers on an outer peripheral portion of the first drum, the first drum being configured to stack a first core portion in the first area;
   a second drum having a plurality of second areas, smaller than the first area, for sucking and stacking the fibers on an outer peripheral portion of the second drum, the second drum being configured to successively transfer second core portions stacked in each of the second areas to the first drum; and
   a variable speed drive configured to rotate the second drum at a high first circumferential velocity when the second drum transfers each of the second core portions and, rotate the second drum at a second circumferential velocity, lower than the first circumferential velocity, in non-transfer time, which is after the transfer and until subsequent transfer.

2. The apparatus for manufacturing an absorbent core according to claim 1, wherein the variable speed drive includes a servomotor configured to rotate the second drum and a controller configured to control the rotation of the servomotor.

3. The apparatus for manufacturing an absorbent core according to claim 2, wherein the feeder has a single defibrator as the defibrator and includes
   a first duct portion configured to gas-transport the fibers generated by the single defibrator to the first drum and
   a second duct portion configured to gas-transport the fibers generated by the single defibrator to the second drum.

4. The apparatus for manufacturing an absorbent core according to claim 2, wherein the controller is configured to control the rotation of the servomotor so that the high first circumferential velocity of the second drum during the transfer is the same as a circumferential velocity of the first drum.

5. The apparatus for manufacturing an absorbent core according to claim 4, wherein the feeder has a single defibrator as the defibrator and includes
   a first duct portion configured to gas-transport the fibers generated by the single defibrator to the first drum and
   a second duct portion configured to gas-transport the fibers generated by the single defibrator to the second drum.

6. The apparatus for manufacturing an absorbent core according to claim 4, wherein the controller is configured to control the rotation of the servomotor so that:
   the high first circumferential velocity during the transfer is a constant circumferential velocity, and
   in the non-transfer time, the rotation of the second drum is decelerated from the first circumferential velocity to the low second circumferential velocity after the transfer and the rotation of the second drum is accelerated from the low second circumferential velocity to the high first circumferential velocity before subsequent transfer.

7. The apparatus for manufacturing an absorbent core according to claim 6, wherein the feeder has a single defibrator as the defibrator and includes
   a first duct portion configured to gas-transport the fibers generated by the single defibrator to the first drum and
   a second duct portion configured to gas-transport the fibers generated by the single defibrator to the second drum.

8. The apparatus for manufacturing an absorbent core according to claim 1, wherein the feeder has a single defibrator as the defibrator and includes
   a first duct portion configured to gas-transport the fibers generated by the single defibrator to the first drum and
   a second duct portion configured to gas-transport the fibers generated by the single defibrator to the second drum.

9. A method of manufacturing an absorbent core for a disposable wearable article by combining a first core portion and a second core portion, the method using
   a feeder having a defibrator configured to generate fibers crushed into a fibrous form and feed the fibers,
   a first drum having a first area for sucking and stacking the fibers on an outer peripheral portion of the first drum, the first drum being configured to stack a first core portion in the first area, and
   a second drum having a plurality of second areas, smaller than the first area, for sucking and stacking the fibers on an outer peripheral portion of the second drum, the second drum being configured to successively transfer second core portions stacked in each of the second areas to the first drum, the method comprising:

a step of stacking the first core portion in the first area;

a step of stacking the second core portions in the second areas;

a step of transferring the second core portions from the second drum onto the first drum;

a step of rotating the second drum at a high first circumferential velocity during the transferring; and a step of rotating the second drum at a second circumferential velocity lower than the first circumferential velocity in non-transfer time.

10. The method of manufacturing an absorbent core according to claim 9, wherein the second drum is rotated so that the high first circumferential velocity of the second drum during the transferring is the same as a circumferential velocity of the first drum.

11. The method of manufacturing an absorbent core according to claim 10, further comprising a step of gas-transporting the fibers generated by a single defibrator through a first duct portion to the first drum and a step of gas-transporting the fibers generated by the single defibrator through a second duct portion to the second drum.

12. The method of manufacturing an absorbent core according to claim 10, wherein the rotation of a servomotor is controlled so that:

the high first circumferential velocity during the transfer is a constant circumferential velocity, and in the non-transfer time, the rotation of the second drum is decelerated from the first circumferential velocity to the low second circumferential velocity after the transfer and the rotation of the second drum is accelerated from the low second circumferential velocity to the high first circumferential velocity before subsequent transfer.

13. The method of manufacturing an absorbent core according to claim 12, further comprising a step of gas-transporting the fibers generated by a single defibrator through a first duct portion to the first drum and a step of gas-transporting the fibers generated by the single defibrator through a second duct portion to the second drum.

14. The method of manufacturing an absorbent core according to claim 9, further comprising a step of gas-transporting the fibers generated by a single defibrator through a first duct portion to the first drum and a step of gas-transporting the fibers generated by the single defibrator through a second duct portion to the second drum.

* * * * *